US010238434B2

(12) United States Patent
Ricica et al.

(10) Patent No.: US 10,238,434 B2
(45) Date of Patent: Mar. 26, 2019

(54) SYSTEM AND METHOD FOR SPINAL DECOMPRESSION

(71) Applicants: Aaron Ricica, Brookline, MA (US); Craig Henshaw, Charlestown, MA (US); Jacob R. Lubinski, Beverly, MA (US)

(72) Inventors: Aaron Ricica, Brookline, MA (US); Craig Henshaw, Charlestown, MA (US); Jacob R. Lubinski, Beverly, MA (US)

(73) Assignee: SPINEFRONTIER, INC, Malden, MA (US)

( * ) Notice: Subject to any disclaimer, the term of this patent is extended or adjusted under 35 U.S.C. 154(b) by 688 days.

(21) Appl. No.: 14/661,211

(22) Filed: Mar. 18, 2015

(65) Prior Publication Data

US 2015/0265317 A1    Sep. 24, 2015

Related U.S. Application Data

(60) Provisional application No. 61/955,892, filed on Mar. 20, 2014.

(51) Int. Cl.
*A61B 17/70* (2006.01)
*A61B 17/02* (2006.01)
*A61B 90/00* (2016.01)

(52) U.S. Cl.
CPC .. *A61B 17/7071* (2013.01); *A61B 2017/0256* (2013.01); *A61B 2090/061* (2016.02)

(58) Field of Classification Search
CPC .................................................. A61B 17/7071
See application file for complete search history.

(56) References Cited

U.S. PATENT DOCUMENTS

| 6,478,800 B1 * | 11/2002 | Fraser ................... A61F 2/4611 606/90 |
| 6,660,007 B2 | 12/2003 | Khanna |
| 8,105,366 B2 | 1/2012 | Null et al. |
| 8,147,528 B2 | 4/2012 | Mazzuca et al. |
| 8,172,875 B2 | 5/2012 | Taylor |
| 8,430,882 B2 | 4/2013 | Lowry et al. |
| 8,470,003 B2 | 6/2013 | Voellmicke et al. |
| 8,480,680 B2 | 7/2013 | Lewis |

(Continued)

FOREIGN PATENT DOCUMENTS

| CN | 104000646 A | 8/2014 |
| EP | 2835113 A2 | 2/2015 |

(Continued)

*Primary Examiner* — Olivia C Chang
(74) *Attorney, Agent, or Firm* — AKC Patents, LLC; Aliki K. Collins

(57) ABSTRACT

A system for performing a laminoplasty procedure in a spinal vertebra includes an implant and an inserter tool. The implant is configured to be placed on a previously formed lamina opening of the spinal vertebra, and is shaped and dimensioned to be placed in the lamina opening after the opening has been distracted. The inserter tool is configured to insert the implant near the lamina opening and then to distract the lamina opening so that the lamina opening is dimensioned to receive the implant and then to place the implant into the distracted lamina opening while simultaneously holding the lamina opening in a distracted state.

20 Claims, 13 Drawing Sheets

(56) References Cited

U.S. PATENT DOCUMENTS

| | | |
|---|---|---|
| 8,518,081 B2 | 8/2013 | Patel et al. |
| 8,562,681 B2 | 10/2013 | Shepard et al. |
| 8,828,057 B1 | 9/2014 | Jamshidi |
| 8,915,946 B2 | 12/2014 | Khanna |
| 8,926,664 B1 | 1/2015 | Millhouse et al. |
| 2002/0072752 A1 | 6/2002 | Zucherman et al. |
| 2009/0240280 A1 | 9/2009 | Wang et al. |
| 2009/0270873 A1 | 10/2009 | Fabian |
| 2011/0060338 A1 | 3/2011 | Kim et al. |
| 2012/0265213 A1 | 10/2012 | Beger et al. |
| 2013/0060283 A1 | 3/2013 | Suh et al. |
| 2013/0197641 A1* | 8/2013 | Shepard .............. A61B 17/7071 623/17.11 |
| 2013/0325022 A1 | 12/2013 | Wright et al. |
| 2014/0172104 A1 | 6/2014 | Dugal et al. |
| 2014/0364917 A1 | 12/2014 | Sandstrom et al. |

FOREIGN PATENT DOCUMENTS

| | | |
|---|---|---|
| JP | 2014147783 A | 8/2014 |
| WO | 2014066890 A1 | 5/2014 |
| WO | 2014078008 A1 | 5/2014 |

\* cited by examiner

Y-direction

X-direction

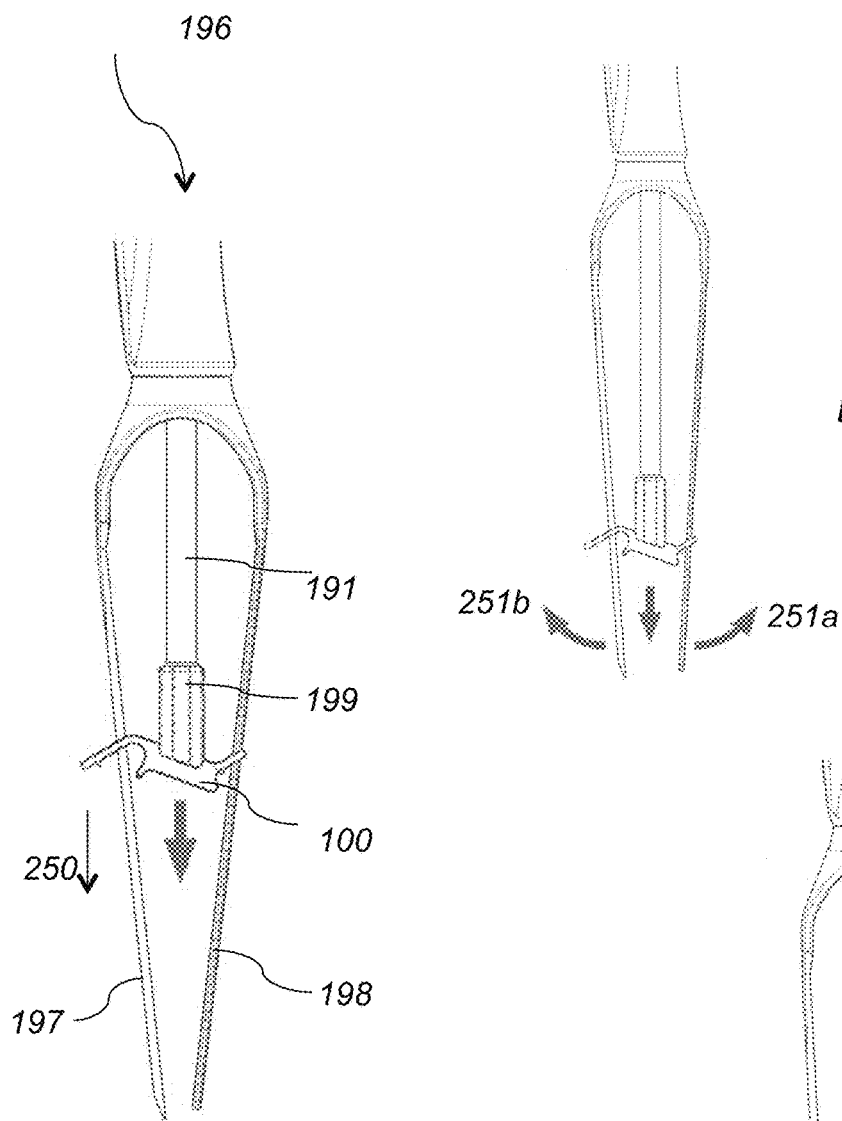
FIG. 8A
FIG. 8B
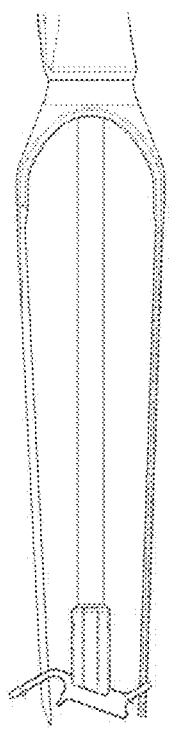
FIG. 8C

SYSTEM AND METHOD FOR SPINAL DECOMPRESSION

CROSS REFERENCE TO RELATED CO-PENDING APPLICATIONS

This application claims the benefit of U.S. provisional application Ser. No. 61/955,892 filed Mar. 20, 2014 and entitled "SYSTEM AND METHOD FOR SPINAL DECOMPRESSION", the contents of which are expressly incorporated herein by reference.

FIELD OF THE INVENTION

The present invention relates to a system and method for spinal decompression, and in particular to laminoplasty fixation devices, tools and methods.

BACKGROUND OF THE INVENTION

Cervical laminoplasty is a surgical technique that is used to remove pressure from the spinal cord in the neck area. Pressure on the spinal cord is usually due to spinal stenosis that may be caused by degenerative changes, arthritis, bone spurs, disc herniations, ossification of the posterior longitudinal ligament (OPLL), tumors, or fractures, among others. Frequently, spinal stenosis occurs simultaneously at multiple levels of the cervical spine. If the pressure is severe enough, myelopathy can develop. In this case, laminoplasty may be applied for removing the pressure, allowing the spinal cord to heal, and reversing the symptoms.

Laminoplasty involves cutting the lamina on both sides of the vertebra and swinging one side of the cut bone away in order to hinge open the spinal canal. This is called the "open door" procedure, where in one side of the lamina a complete through-cut is performed and in the other side a groove or partial cut is formed and the lamina is then hinged opened about the groove in order to increase the diameter of the spinal canal and remove the applied pressure on the spinal cord. Part of the lamina and/or the spinous process may be removed during laminoplasty. The hinged lamina is supported in the open position via a plate that is inserted and fixed between the facet and the cut end of the lamina.

Typically, the surgeon needs to determine the size of the opening and the size of the plate to use in order to increase the diameter of the spinal canal sufficiently so that the pressure on the spinal cord is removed. Flexibility in the size and the overall dimensions of the plate is desirable in order to accommodate various size vertebras.

SUMMARY OF THE INVENTION

The present invention relates to a system and a method for spinal decompression, and in particular to laminoplasty fixation devices, tools and methods.

In general, in one aspect, the invention features a system for performing a laminoplasty procedure in a spinal vertebra, including an implant and an inserter tool. The implant is configured to be placed on a previously formed lamina opening of the spinal vertebra, and is shaped and dimensioned to be placed in the lamina opening after the opening has been distracted. The inserter tool is configured to insert the implant near the lamina opening and then to distract the lamina opening so that the lamina opening is dimensioned to receive the implant and then to place the implant into the distracted lamina opening while simultaneously holding the lamina opening in a distracted state.

Implementations of this aspect of the invention may include one or more of the following features. The implant comprises an elongated body having first second and third segments and the first and third segments extend in opposite directions from opposite ends of the second segment and form first and second angles with an axis extending along the second segment, respectively. The implant further includes a first elongated opening formed in the first segment and the first elongated opening extends along a first axis and comprises an oval shape and is dimensioned to hold a bone fastener in two different locations of the first elongated opening or two bone fasteners in the two different locations of the first elongated opening, respectively. The implant further includes a second elongated opening formed in the third segment and the second elongated opening extends perpendicular to the first axis and comprises an oval shape and is dimensioned to hold a bone fastener in two different locations of the second elongated opening or two bone fasteners in the two different locations of the second elongated opening, respectively. The implant further includes a ledge extending from the second segment and being shaped and dimensioned to surround the lamina. The implant further includes a trough formed in the second segment and designed to accommodate bonegraft. The inserter tool comprises an elongated shaft and a distal end and the distal end includes first and second spreadable shims. The first and second spreadable shims are shaped and dimensioned to pass through first and second openings formed in the implant and the implant is configured to slide down along the first and second shims by pushing the elongated shaft down and to spread the first and second shims apart. The first and second ends of the first and second shims are configured to engage first and second locations within or near the lamina opening, respectively, and to distract the lamina opening as they spread apart. At least one of the first and second ends of the first and second shims comprises a hook. The elongated shaft includes a distal end component configured to engage the implant. The inserter tool further includes a handle attached to a proximal end of the shaft and activation of the handle pushes the elongated shaft down or up.

In general in another aspect the invention features a method for performing a laminoplasty procedure in a spinal vertebra, including the following. Providing an implant configured to be placed on a previously formed lamina opening of the spinal vertebra. The implant is shaped and dimensioned to be placed in the lamina opening after the opening has been distracted. Providing an inserter tool configured to insert the implant near the lamina opening and then to distract the lamina opening so that the lamina opening is dimensioned to receive the implant and then to place the implant into the distracted lamina opening while simultaneously holding the lamina opening in a distracted state. The inserter tool comprises an elongated shaft and a distal end and the distal end has first and second spreadable shims. The first and second spreadable shims are shaped and dimensioned to pass through first and second openings formed in the implant and the implant is configured to slide down along the first and second shims by pushing the elongated shaft down and to spread the first and second shims apart.

BRIEF DESCRIPTION OF THE DRAWINGS

Referring to the figures, wherein like numerals represent like parts throughout the several views:

FIG. 8A-FIG. 8C depict the shimmed implant inserter of FIG. 7A, as used in a spinal decompression method, according to this invention.

DETAILED DESCRIPTION OF THE INVENTION

The present invention relates to a system and method for spinal decompression, and in particular to laminoplasty fixation devices, tools and methods.

Laminoplasty is usually performed via a posterior approach. During surgery, the patient lies face down on the operating table and an incision is made in the back of the neck. In the "open door" laminoplasty procedure, instead of removing the lamina and other compressive structures, the lamina is completely through-cut on one side between the lamina and the lateral mass and partially cut on the opposite lateral side. This creates a hinge on the partial cut side of the lamina and a small opening on the opposite lateral side. The lamina is then moved into the "open" position by elevating the lamina on the open side. This increases the diameter of the spinal canal and makes space available for the spinal cord. The spinal cord is decompressed and the spinal fluid can flow around the spinal cord. A plate or a wedge made out of bone, metal, or plastic, is usually inserted in the open side to hold the spinal canal open. The final position resembles an open door being held open with a door stop, and therefore the procedure is referred to as an "open-door" laminoplasty.

Figure 1A:
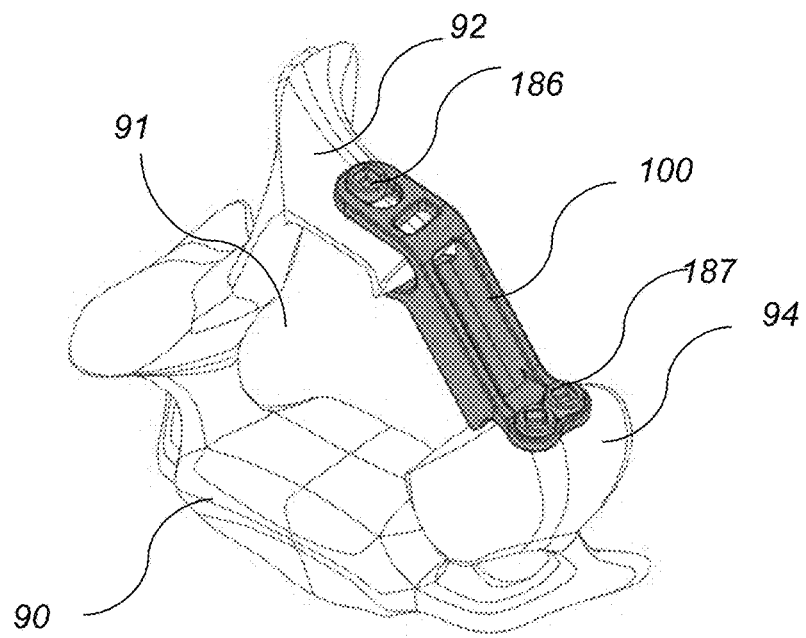
FIG. 1A depicts one embodiment of the graft plate, according to this invention.
Figure 1B:
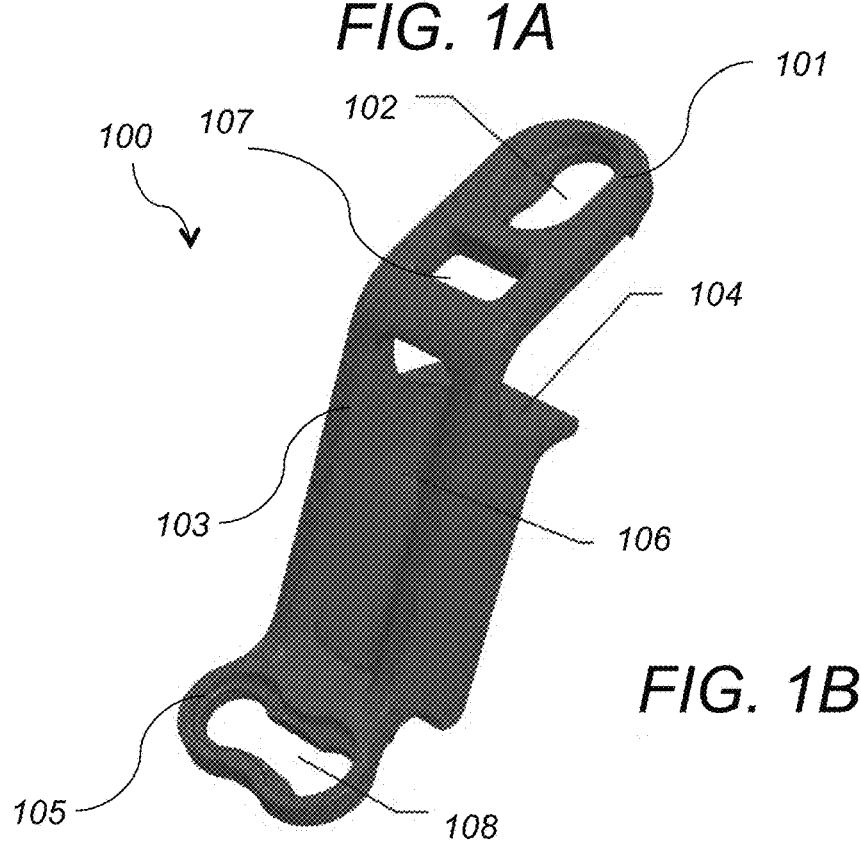
FIG. 1B is a perspective view of the embodiment of FIG. 1A.
Figure 1C:
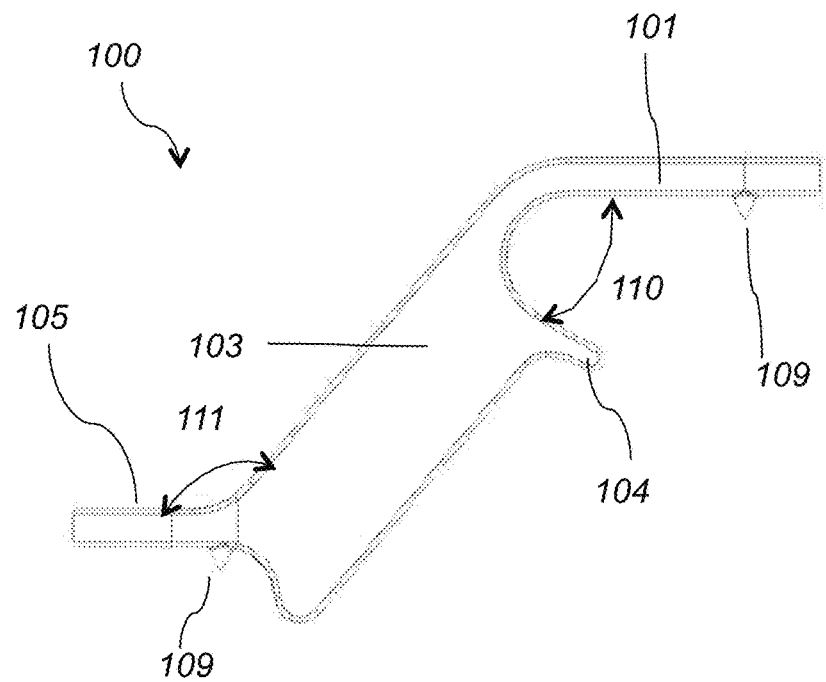
FIG. 1C is a side view of the embodiment of FIG. 1A.
Figure 1D:
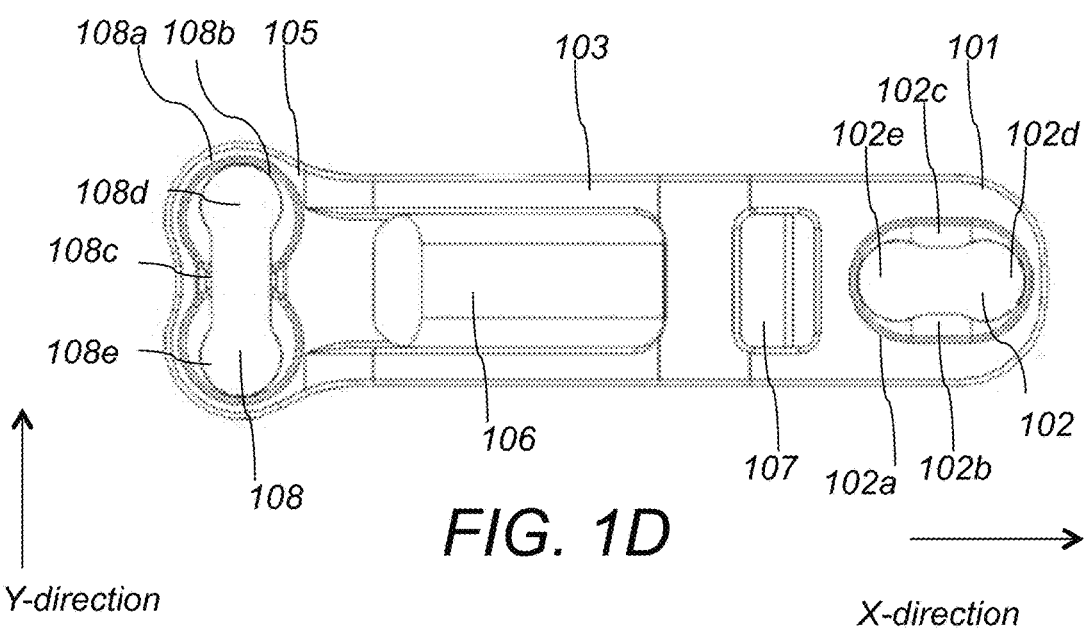
FIG. 1D is a top view of the embodiment of FIG. 1A.

Referring to FIG. 1A-FIG. 1D, graft plate 100 creates a brace between the lamina 92 and the lateral mass 94 of the posterior of vertebra 90. In doing so, the diameter of the inner canal space 91 for that particular segment is opened up and this relieves congestion and compression in the spinal canal. Graft plate 100 includes an elongated body having a first segment 101, a second segment 103 and a third segment 105. First and third segments 101, 105, extend in opposite directions from the second segment 103 and form angles 110 and 111, with the second segment, respectively. First segment 101 includes an elongated opening 102 extending along axis x and being designed to hold two bone fasteners in two separate positions or one bone fastener in two different positions. As shown in FIG. 1D, opening 102 includes an oval-shaped outer perimeter 102a and an inner perimeter 102b having an oval shape with a constricted center 102c. Through the circular ends 102d, 102e of the inner perimeter 102b, two separate bone fasteners can pass through in order to attach the graft plate 100 to the lamina. Alternatively, one bone fastener passes either through end 102d or through end 102e in order to attach the graft plate to two different positions of the lamina, thereby increasing or decreasing the diameter of the canal space 91. First segment 101 also includes a rectangular opening 107 dimensioned to engage a shimmed inserter tool, as will be described below. The second segment 103 includes a ledge 104 to surround the lamina and lodge it into the optimal plate position, and a trough 106 designed to accommodate different forms of bonegraft, such as cancellous sponge, chips, demineralized bone matrix (dbm), or synthetic bonegraft. Bonegraft facilitates blood flow and promotes bone ingrowth for healing. Third segment 105 includes an elongated opening 108 extending along axis y perpendicular to axis x of opening 102 and being designed to hold two bone fasteners in two separate positions or one bone fastener in two different positions. As shown in FIG. 1D, opening 108 includes oval-shaped outer and inner perimeters 108a, 108b having a constricted center 108c. Through the circular ends 108d, 108e of the inner perimeter 108b, two separate bone fasteners can pass through in order to attach the graft plate 100 to the lateral mass 94. Alternatively, one bone fastener passes either through end 108d or through end 108e in order to attach the graft plate to two different positions of the lateral mass 94. First and third segments 101, 105 also include spikes or serrations 109 used for engaging the graft plate 100 to the lamina 92 and the lateral mass 94, respectively.

Figure 2A:
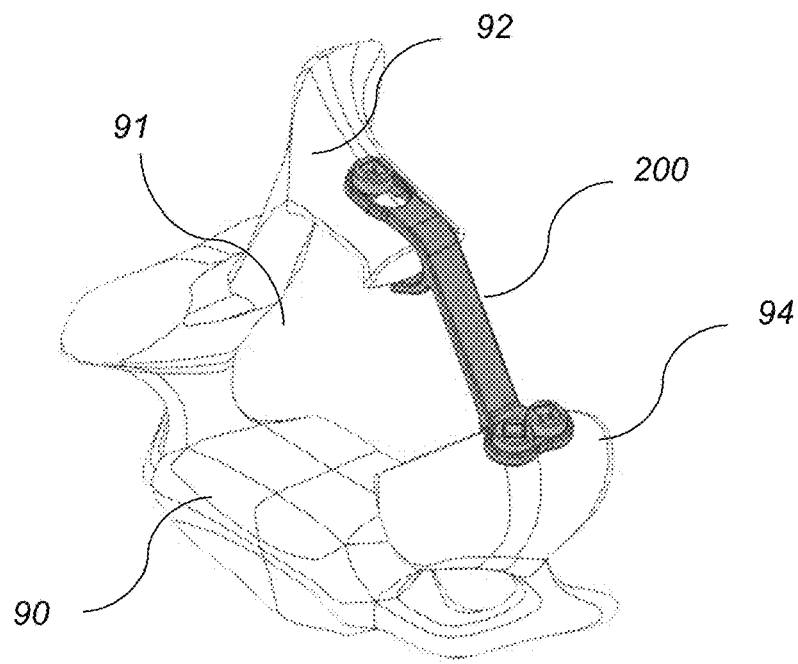
FIG. 2A depicts another embodiment of the graft plate, according to this invention.
Figure 2B:
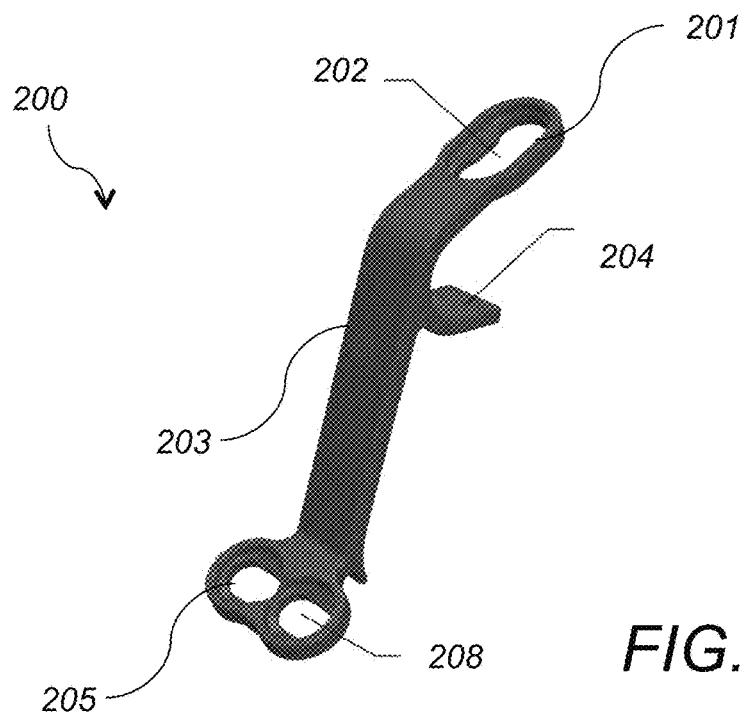
FIG. 2B is a perspective view of the embodiment of FIG. 2A.
Figure 2C:
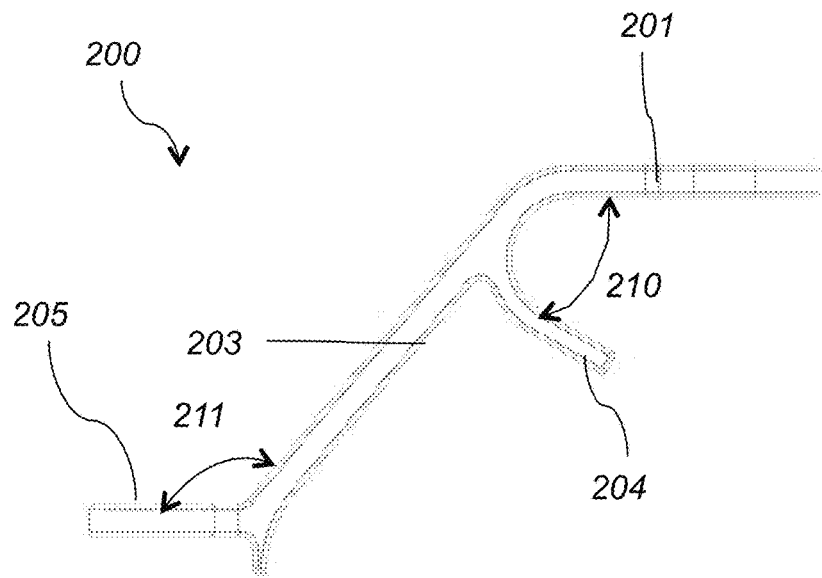
FIG. 2C is a side view of the embodiment of FIG. 2A.
Figure 2D:
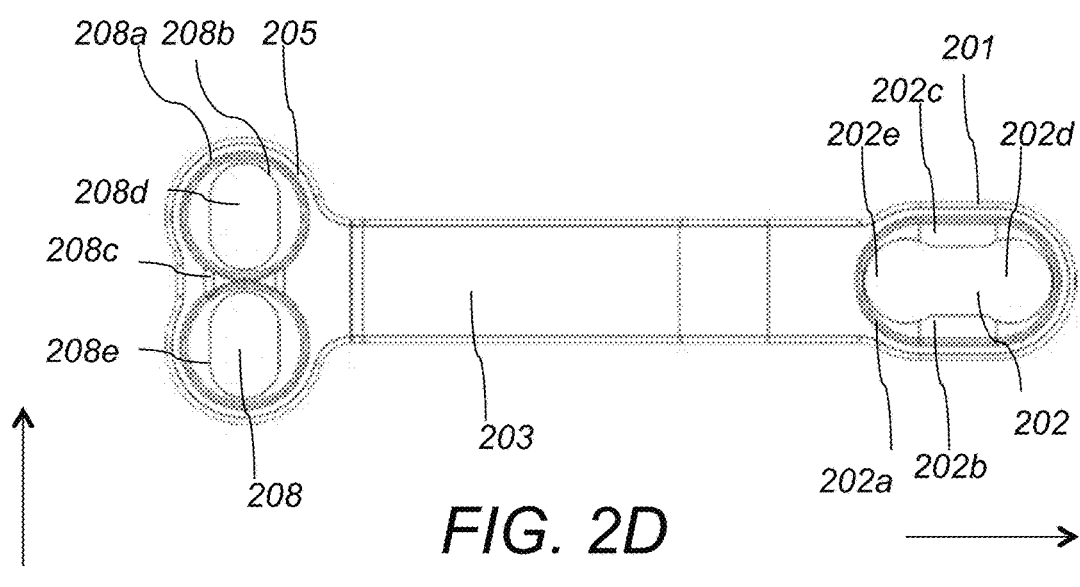
FIG. 2D is a top view of the embodiment of FIG. 2A.
Figure 3A:
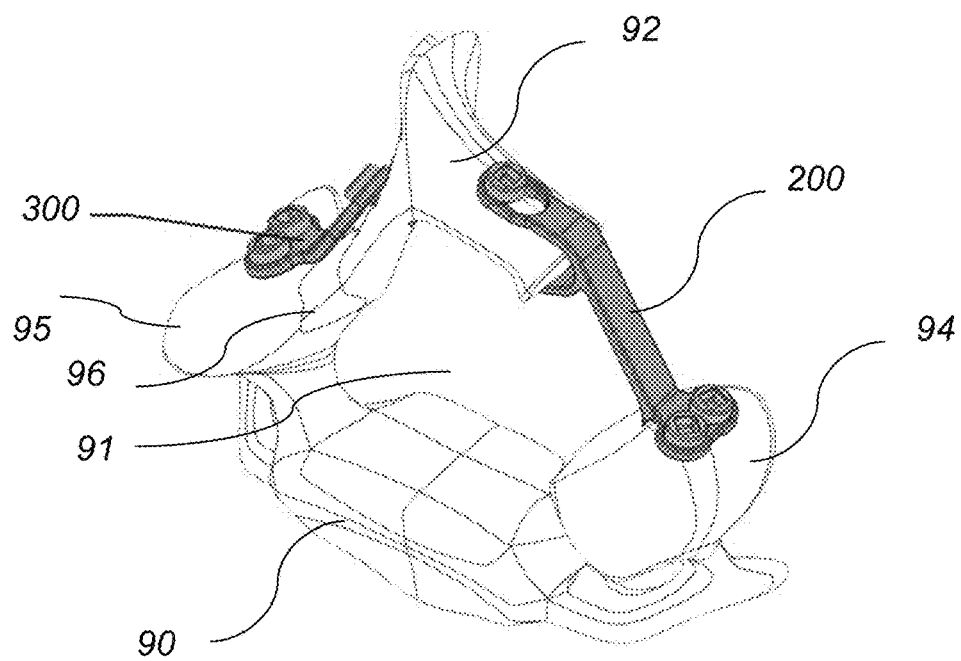
FIG. 3A depicts an embodiment of a hinge plate, according to this invention.
Figure 3B:
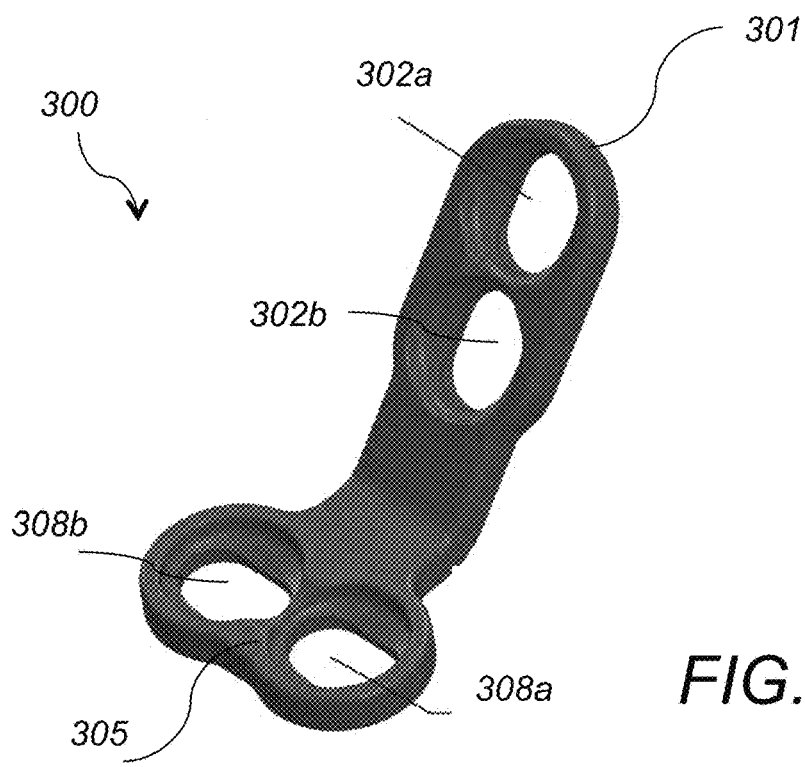
FIG. 3B is a perspective view of the embodiment of FIG. 3A.
Figure 3C:
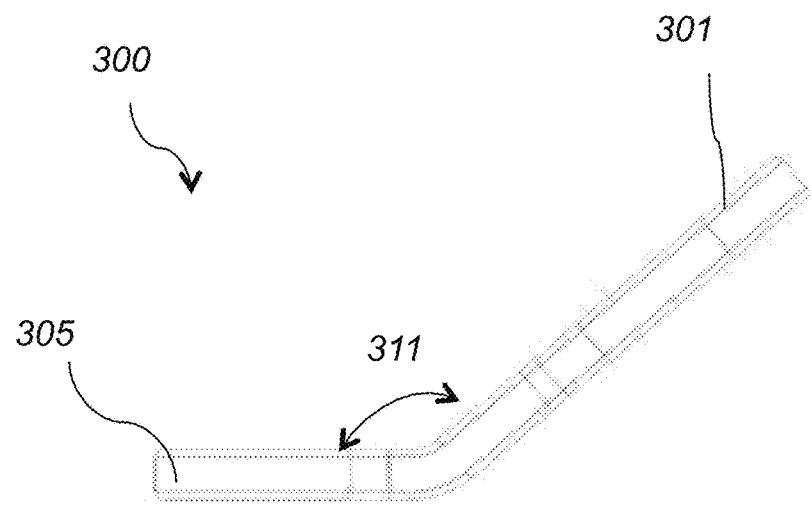
FIG. 3C is a side view of the embodiment of FIG. 3A.
Figure 3D:
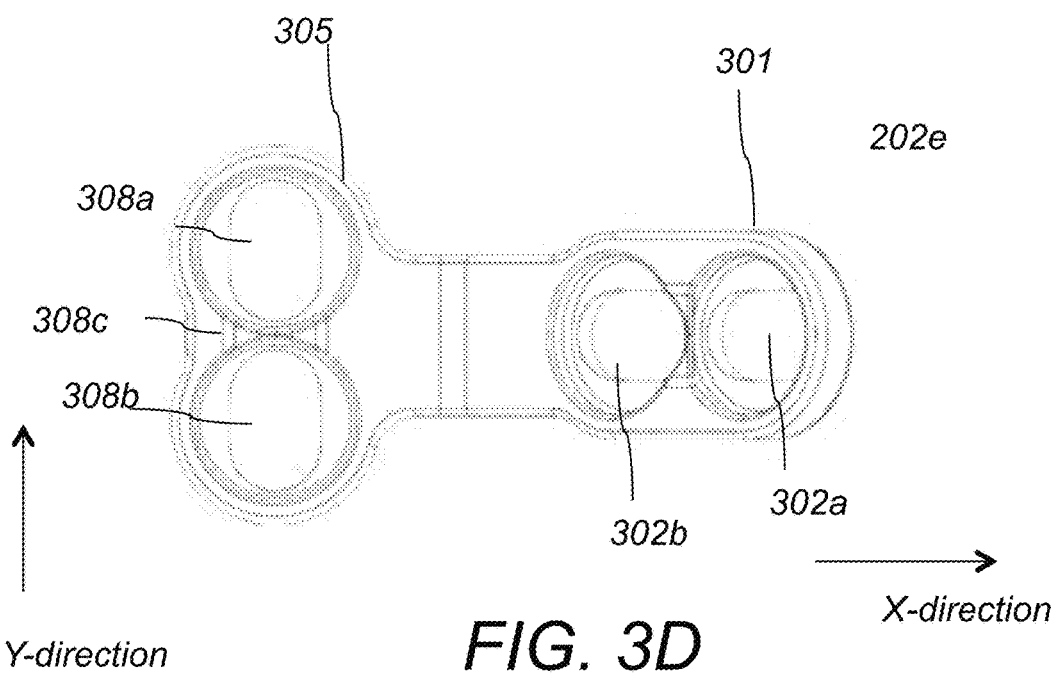
FIG. 3D is a top view of the embodiment of FIG. 3A.

Referring to FIG. 2A-FIG. 2D, in another embodiment, plate 200 creates a brace between the lamina 92 and the lateral mass 94 of the posterior of vertebra 90. In doing so, the diameter of the inner canal space 91 for that particular segment is opened up and this relieves congestion and compression in the spinal canal. Plate 200 includes an elongated body having a first segment 201, a second segment 203 and a third segment 205. First and third segments 201, 205, extend in opposite directions from the second segment 203 and form angles 210 and 211, with the second segment, respectively. First segment 201 includes an elongated opening 202 extending along axis x and being designed to hold two bone fasteners in two separate positions or one bone fastener in two different positions. As shown in FIG. 2D, opening 202 includes an oval-shaped outer perimeter 202a and an inner perimeter 202b having an oval shape with a constricted center 202c. Through the circular ends 202d, 202e of the inner perimeter 202b, two separate bone fasteners can pass through in order to attach the plate 200 to the lamina. Alternatively, one bone fastener passes either through end 202d or through end 202e in order to attach the plate 200 to two different positions of the lamina, thereby increasing or decreasing the diameter of the canal space 91. Second segment 203 includes a ledge 204 designed to surround the lamina and lodge it into the optimal plate position. Third segment 205 includes an elongated opening 208 extending along axis y perpendicular to axis x of opening 202 and being designed to hold two bone fasteners in two separate positions or one bone fastener in two different positions. As shown in FIG. 2D, opening 208 includes oval-shaped outer and inner perimeters 208*a*, 208*b* having a constricted center 208*c*. Through the circular ends 208*d*, 208*e* of the inner perimeter 208*b*, two separate bone fasteners can pass through in order to attach the plate 200 to the lateral mass 94. Alternatively, one bone fastener passes either through end 208*d* or through end 208*e* in order to attach the plate to two different positions of the lateral mass 94.

In some cases, a plate is also used to support the hinged side of the lamina. Referring to FIG. 3A-FIG. 3D, in another embodiment, plate 200 creates a brace between the lamina 92 and the lateral mass 94 of the posterior of vertebra 90 and a hinge plate 300 is fixed to the opposite side of plate 200 or graft plate 100 and is used to secure the contra-lateral lamina. This lamina 92 in this case is burred to help create the pivot. The burring process may weaken the lamina and the hinge plate 300 strengthens the pivot. Hinge plate 300 is placed between the lamina 92 and lateral mass 95 at the treated area that creates the pivot point 96. Hinge plate 300 includes an elongated body having a first segment 301 and a second segment 305. Second segment 305 forms an angle 311, with the first segment 301. First segment 301 includes two adjacent through-openings 302*a*, 302*b*. Openings 302*a*, 302*b* have round shaped outer diameters and oval-shaped inner diameters extending along axis x. Two separate bone fasteners pass through the circular openings 302*a*, 302*b* in order to attach the hinge plate 300 to the lamina 92. Second segment 305 includes two adjacent openings 308*a*, 308*b* arranged along axis y perpendicular to axis x, and a constricted center 308*c*. Openings 308*a*, 308*b* have round shaped outer diameters and oval-shaped inner diameters extending along axis y. Two separate bone fasteners pass through the circular openings 308*a*, 308*b* in order to attach the hinge plate 300 to the lateral mass 95.

Figure 4A:
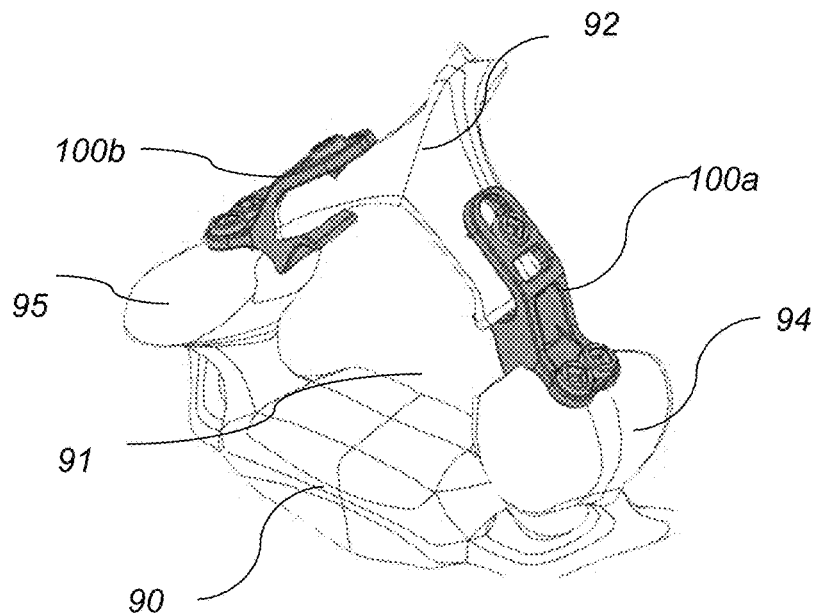
FIG. 4A and FIG. 4B depict an embodiment where bilateral graft plates are used to stabilize the lamina, according to this invention.
Figure 4B:
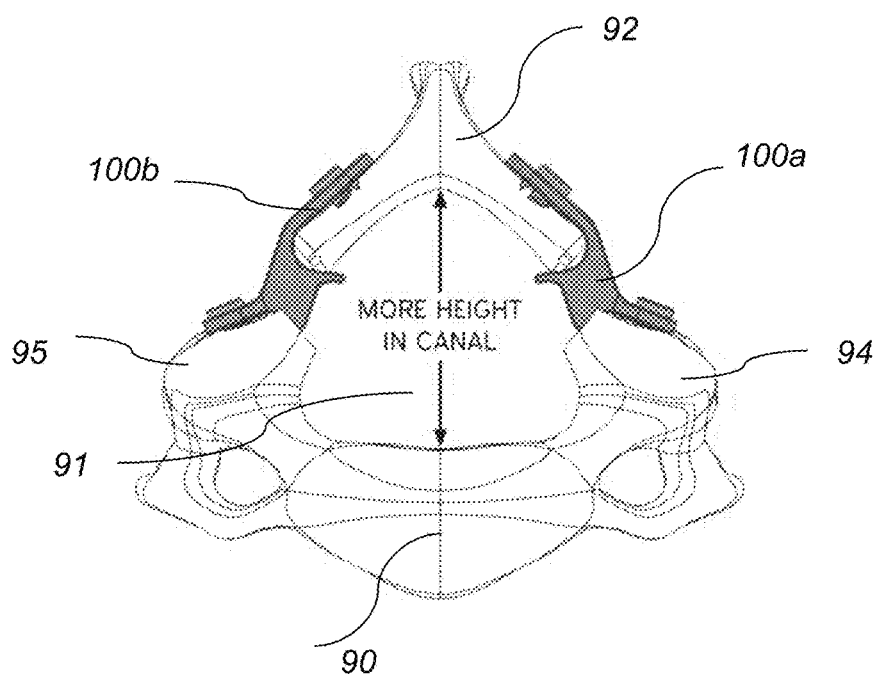

In another embodiment, bilateral graft plates are used to support the lamina. Referring to FIG. 4A and FIG. 4B, graft plates 100*a*, 100*b* are used to support the lamina to the lateral masses 94, 95, respectively. In this configuration the height of the spinal canal 91 is increased and there is no pivoting of the lamina.

Figure 5:
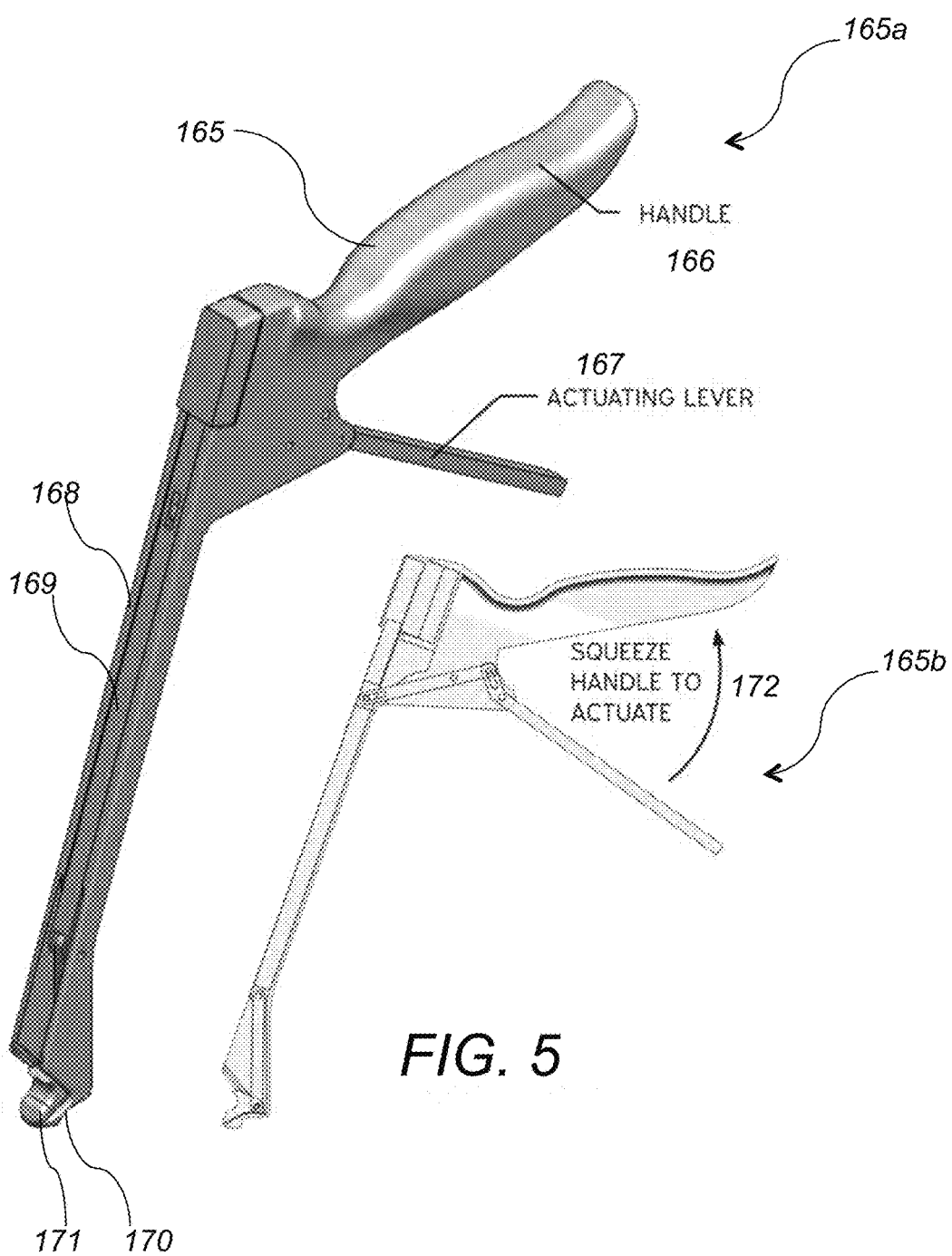
FIG. 5 depicts an embodiment of a distractor sizer in the closed and open positions, according to this invention.
Figure 5A:
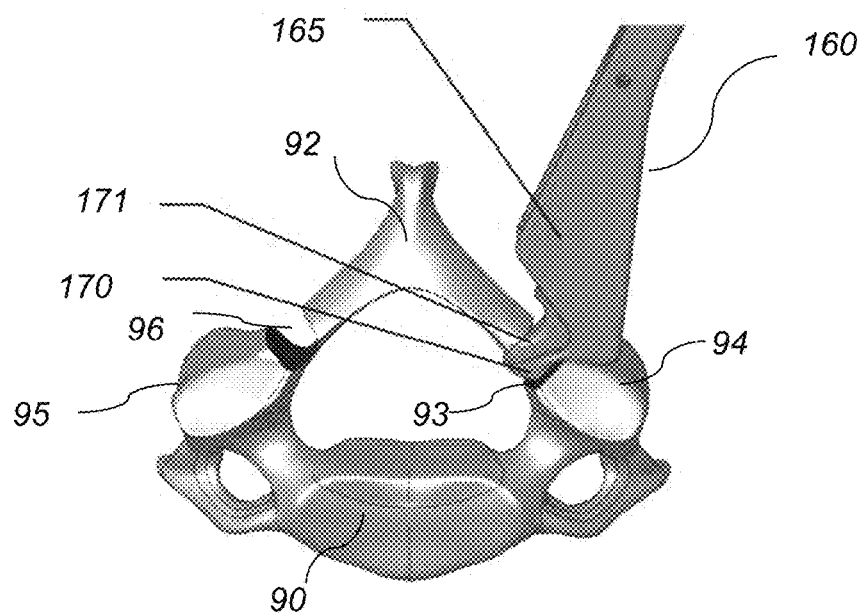
FIG. 5A and FIG. 5B depict the use of the distractor sizer of FIG. 5 in the process of distracting the cut lamina.
Figure 5B:
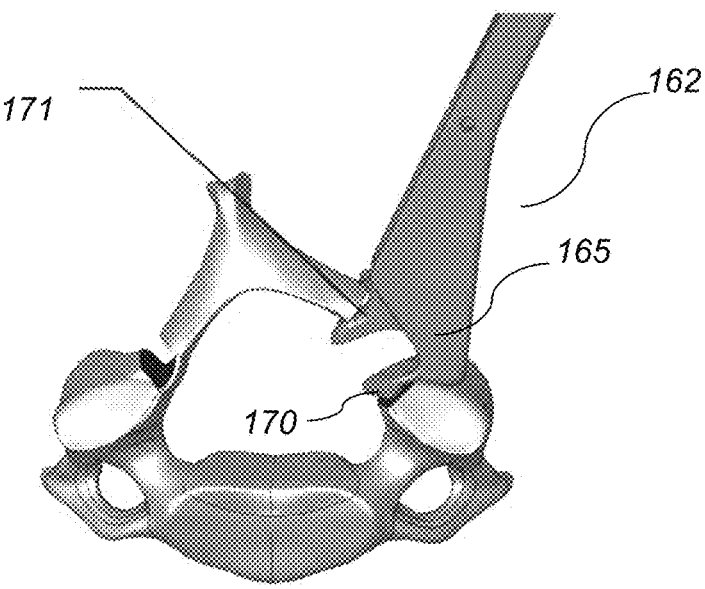

In operation, the lamina 92 is completely cut-through on one side 93 between the lamina 92 and the lateral mass 94 and partially cut 96 on the opposite lateral side 95, as shown in FIG. 5A and FIG. 5B. This creates a hinge on the partial cut side 96 of the lamina 92 and a small opening 93 on the opposite lateral side 94. The lamina 92 is then moved into the "open" position by elevating the lamina on the open side 93, as shown in FIG. 5B. In one embodiment, the lamina 92 is distracted posteriorly into the "open" position 165*a* by inserting a distractor sizer tool 165 between the lamina 92 and the lateral mass 94, shown in FIG. 5. Referring to FIG. 5, distractor sizer 165 is a surgical instrument used to distract the height between the burred lamina 92 and the lateral mass 94. Distractor sizer 165 is also used to read the correct height of expansion and to determine the correct measurement of graft plate or standard plate to use in this procedure. This distractor sizer 165 includes an outer shaft 168 surrounding an inner shaft 169 from proximal to distal ends, a top spreader 171 and a bottom spreader 170 at the distal end, a handle 166 and an actuating lever 167 at the proximal end. The distractor sizer spreaders 170, 171 are inserted between the lamina and the lateral mass to distract the lamina posteriorly, and then the actuating lever 172 is pulled back along arrow 172 to advance the inner shaft 169 distally and thereby to activate the top spreader 171 and distract the lamina posteriorly. Next, the graft plate 100 is inserted in the opening between the distracted lamina and the lateral mass.

Figure 6A:
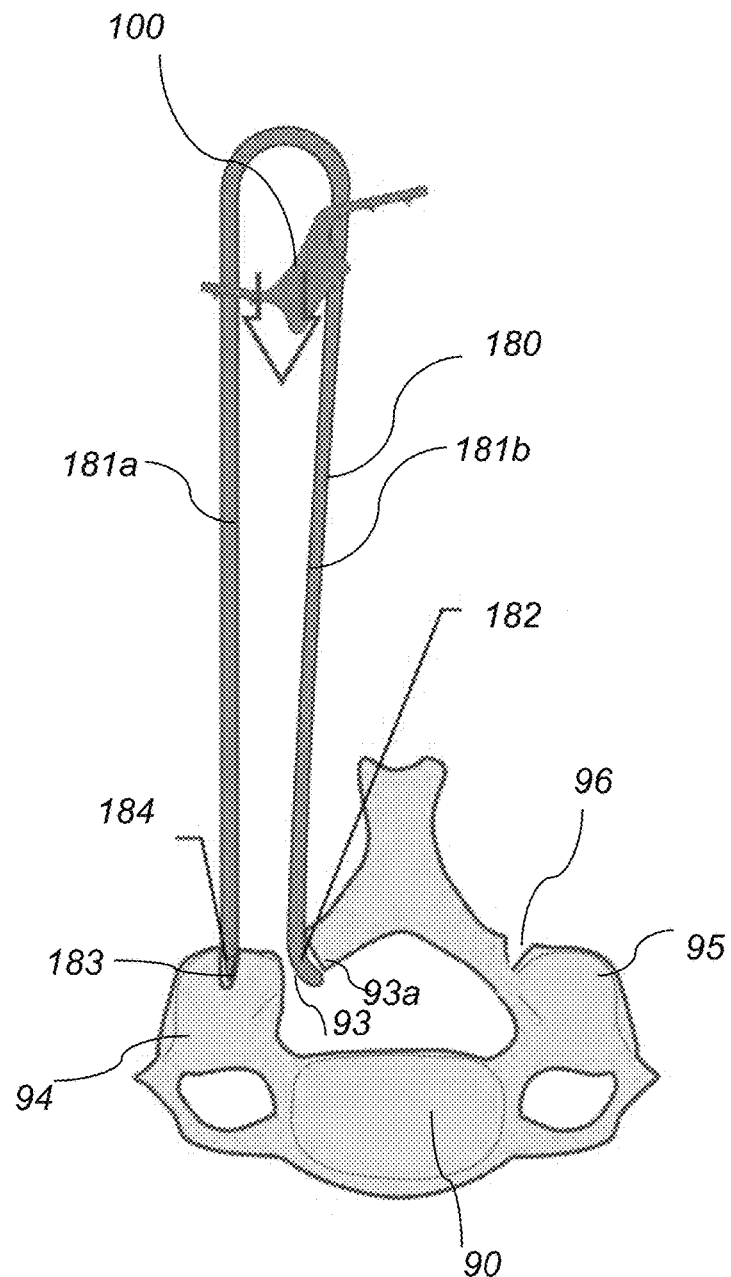
FIG. 6A-FIG. 6C depicts the shimmed inserter method for spinal decompression according to this invention.
Figures 6B, 6C:
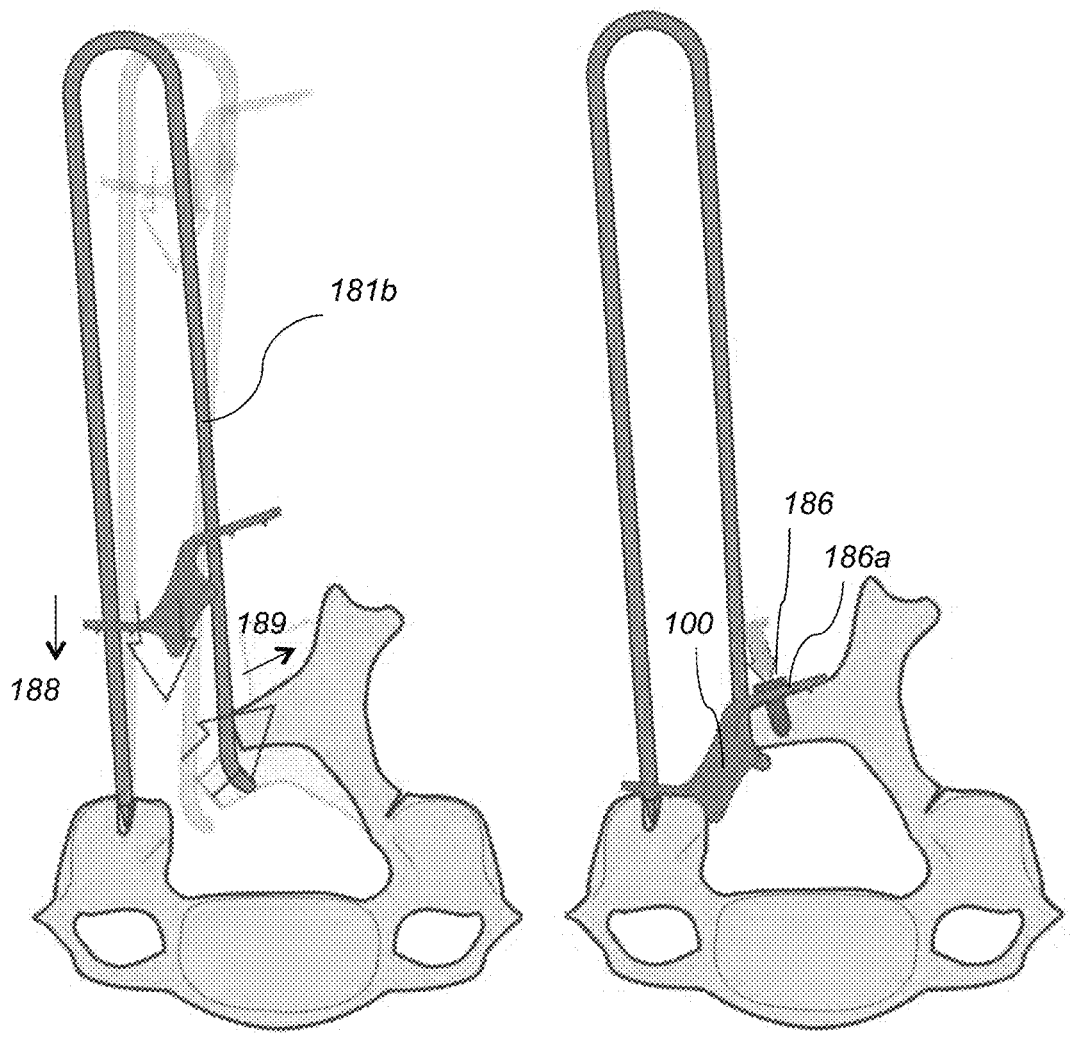
Figure 7B:
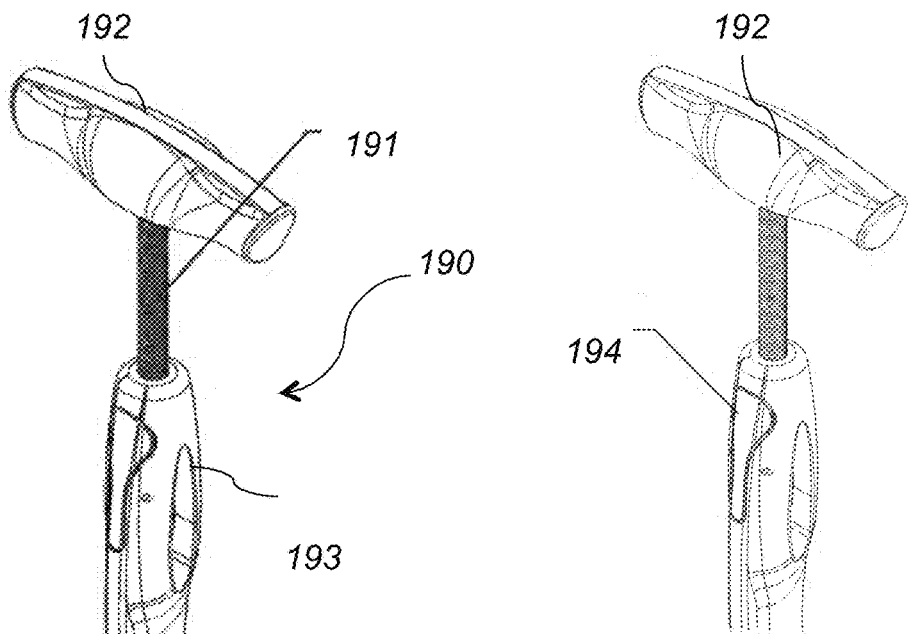
FIG. 7B depicts the proximal end of the shimmed implant inserter of FIG. 7A.
Figure 7A:
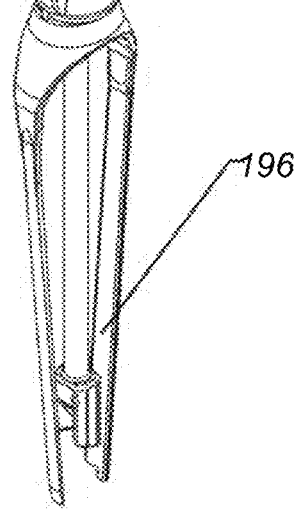
FIG. 7A depicts a shimmed implant inserter, according to this invention.
Figure 7C:
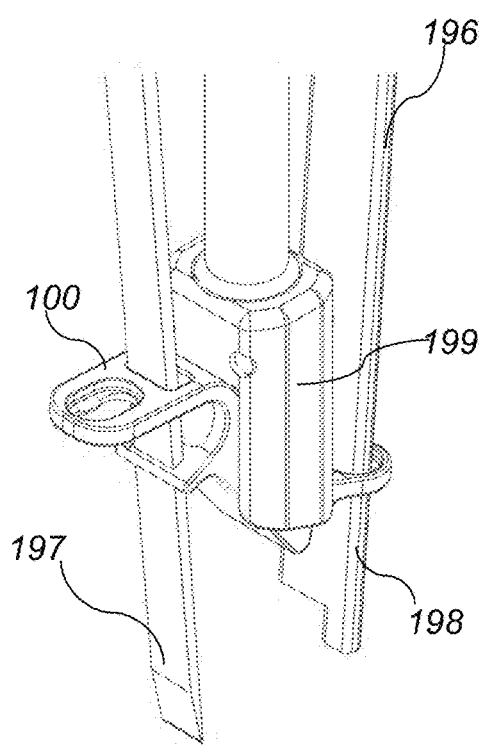
FIG. 7C depicts the distal end of the shimmed implant inserter of FIG. 7A.

Referring to FIG. 6A-FIG. 6C, the shimmed inserter method describes a technique for inserting a graft plate 100 or a standard plate 200 or bilateral graft plate 100*a* onto the surgical site while keeping the lamina distraction intact. The method utilizes a shimmed inserter 180 to insert one of either the standard plate 100, graft plate 200, or a bilateral graft plate 100*a*, 100*b*. The shimmed inserter tool 180 includes a U-shaped body 181 having an open lateral mass end 184 and a hook end 182. The legs 181*a*, 181*b* of the U-shaped body 181 have cross-section matching the cross-sections of openings 107 and 108 of the graft plate. Legs 181*a*, 181*b* are inserted into openings 107 and 108 of the graft plate and 100 the graft plate 100 is moved toward the proximal closed end of the U-shaped body 181 of the shimmed inserter 180, as shown in FIG. 6A. After drilling screw holes 186*a* in the lamina and after burring the lamina, the shimmed inserter lateral mass end 184 is placed in a pre-drilled hole 183 on the lateral mass 94 and the hook end 182 is placed under the cut lamina end 93*a*, as shown in FIG. 6A. Next, leg 181*b* is pulled laterally along direction 180 to pry open and distract the lamina 92 and then the graft plate 100 is pressed down along direction 188 and is placed in the opening 93 between the cut end 93*a* of the lamina and the lateral mass 94. Next, the graft plate 100 is secured onto the lamina 92 and the lateral mass 94 distally with setscrews 186, 187, respectively, after the shimmed inserter is removed.

Referring to FIG. 7A-FIG. 8C, in another embodiment a shimmed inserter 190 is used to distract the distance in the burred void 93 between the lateral mass 94 and lamina 92. Shimmed inserter 190 includes a t-handle 192, an shaft 191 which drives down the implant 100 distally, and a distal end 196 including two shims 197, 198 which spread out as the plate 100 is advanced down along axis 250. The shims 197, 198 have cross-sections matching the cross-sections of openings 107 and 108 of the graft plate 100. Shims 197, 198 are inserted into openings 107 and 108 of the graft plate and 100 the graft plate 100 is moved down along axis 120 by rotating the handle 192 and thereby advancing the shaft 191 down, as shown in FIG. 8A. The distal end of shaft 191 includes an end component 199 that is designed to engage the body of the graft plate 100. Shimmed inserter 190 also includes a spring lock 193 that in locked position allows shaft 191 to travel proximally without rotating. Initially, the implant 100 is at the top position and the shims 197, 198 are at rest and face inward, as shown in FIG. 8A. Next, the implant 100 is advanced distally, and the shims spread outward forcing the laminal void open, as shown in FIG. 8B. With the implant 100 fully in place, the shims 197, 198, have pried the lamina fully open and the implant 100 is anchored to the bone. In all these embodiments, the inserters both size the lamina opening 93 to match the length of the implant 100 and insert the implant in place.

Several embodiments of the present invention have been described. Nevertheless, it will be understood that various modifications may be made without departing from the spirit and scope of the invention. Accordingly, other embodiments are within the scope of the following claims.

What is claimed is:

1. A system for performing a laminoplasty procedure in a spinal vertebra, comprising:
    an implant configured to be placed on a previously formed lamina opening between a lamina and a lateral mass of the spinal vertebra, wherein the implant is shaped and dimensioned to be placed in the lamina opening after the opening has been distracted;

an inserter tool configured to insert the implant near the lamina opening and then to distract the lamina opening prior to inserting the implant into the lamina opening so that the lamina opening is dimensioned to receive the implant and the inserter tool is configured to then place the implant into the distracted lamina opening while simultaneously holding the lamina opening in a distracted state;

wherein the inserter tool comprises an elongated shaft and a distal end and wherein the distal end comprises first and second spreadable shims and wherein the first and second spreadable shims are shaped and dimensioned to pass through first and second openings formed in the implant, wherein the first and second spreadable shims have cross-sections matching cross-sections of the first and second openings, respectively, and wherein the implant is configured to slide down along the first and second shims by advancing the elongated shaft down and to spread the first and second shims apart.

2. The system of claim 1 wherein the implant comprises an elongated body having first, second and third segments and wherein the first and third segments extend in opposite directions from opposite ends of the second segment and form first and second angles with an axis extending along the second segment, respectively.

3. The system of claim 2, wherein the implant further comprises a first elongated opening formed in the first segment and wherein the first elongated opening extends along a first axis and comprises an oval shape and is dimensioned to hold a bone fastener in two different locations of the first elongated opening or two bone fasteners in the two different locations of the first elongated opening, respectively.

4. The system of claim 3, wherein the implant further comprises a second elongated opening formed in the third segment and wherein the second elongated opening extends perpendicular to the first axis and comprises an oval shape and is dimensioned to hold a bone fastener in two different locations of the second elongated opening or two bone fasteners in the two different locations of the second elongated opening, respectively.

5. The system of claim 2, wherein the implant further comprises a ledge extending from the second segment and being shaped and dimensioned to surround the lamina.

6. The system of claim 2, wherein the implant further comprises a trough formed in the second segment and designed to accommodate bone graft.

7. The system of claim 1, wherein the inserter tool further comprises a spring lock that in a locked position allows the elongated shaft to travel proximally without rotating.

8. The system of claim 7, wherein first and second ends of the first and second shims are configured to engage first and second locations within or near the lamina opening, respectively, and to distract the lamina opening as they spread apart.

9. The system of claim 8, wherein at least one of the first and second ends of the first and second shims comprises a hook.

10. The system of claim 7 wherein the elongated shaft comprises a distal end component configured to engage the implant.

11. The system of claim 7, wherein the inserter tool further comprises a handle attached to a proximal end of the shaft and wherein activation of the handle advances the elongated shaft down or up.

12. A method for performing a laminoplasty procedure in a spinal vertebra, comprising:

providing an implant configured to be placed on a previously formed lamina opening between a lamina and a lateral mass of the spinal vertebra, wherein the implant is shaped and dimensioned to be placed in the lamina opening after the opening has been distracted;

providing an inserter tool configured to insert the implant near the lamina opening and then to distract the lamina opening prior to inserting the implant into the lamina opening so that the lamina opening is dimensioned to receive the implant and the inserter tool is configured to then place the implant into the distracted lamina opening while simultaneously holding the lamina opening in a distracted state; and wherein the inserter tool comprises an elongated shaft and a distal end and wherein the distal end comprises first and second spreadable shims and wherein the first and second spreadable shims are shaped and dimensioned to pass through first and second openings formed in the implant, wherein the first and second spreadable shims have cross-sections matching cross-sections of the first and second openings, respectively, and wherein the implant is configured to slide down along the first and second shims by advancing the elongated shaft down and to spread the first and second shims apart.

13. The method of claim 12, wherein the implant comprises an elongated body having first, second and third segments and wherein the first and third segments extend in opposite directions from opposite ends of the second segment and form first and second angles with an axis extending along the second segment, respectively.

14. The method of claim 13, wherein the implant further comprises a first elongated opening formed in the first segment and wherein the first elongated opening extends along a first axis and comprises an oval shape and is dimensioned to hold a bone fastener in two different locations of the first elongated opening or two bone fasteners in the two different locations of the first elongated opening, respectively.

15. The method of claim 14, wherein the implant further comprises a second elongated opening formed in the third segment and wherein the second elongated opening extends perpendicular to the first axis and comprises an oval shape and is dimensioned to hold a bone fastener in two different locations of the second elongated opening or two bone fasteners in the two different locations of the second elongated opening, respectively.

16. The method of claim 13, wherein the implant further comprises a ledge extending from the second segment and being shaped and dimensioned to surround the lamina.

17. The method of claim 13, wherein the implant further comprises a trough formed in the second segment and designed to accommodate bone graft.

18. The method of claim 12, wherein the inserter tool further comprises a spring lock that in a locked position allows the elongated shaft to travel proximally without rotating.

19. The method of claim 18, wherein first and second ends of the first and second shims are configured to engage first and second locations within or near the lamina opening, respectively, and to distract the lamina opening as they spread apart.

20. The method of claim 18, wherein at least one of the first and second ends of the first and second shims comprises a hook.

* * * * *